(12) United States Patent
Prachumsri et al.

(10) Patent No.: US 7,781,186 B2
(45) Date of Patent: Aug. 24, 2010

(54) SCREENING METHODS USING NORMAL HUMAN LIVER CELL LINE

(75) Inventors: Jetsumon Prachumsri, Samutprakarn (TH); Nongnuch Yimamnuaychok, Thonburi BKK (TH)

(73) Assignee: The United States of America as represented by the Secretary of the Army, Washington, DC (US)

( * ) Notice: Subject to any disclaimer, the term of this patent is extended or adjusted under 35 U.S.C. 154(b) by 891 days.

(21) Appl. No.: 11/335,352

(22) Filed: Jan. 19, 2006

(65) Prior Publication Data

US 2006/0160216 A1 Jul. 20, 2006

Related U.S. Application Data

(63) Continuation-in-part of application No. 09/962,364, filed on Sep. 25, 2001, now Pat. No. 7,015,036.

(60) Provisional application No. 60/235,051, filed on Sep. 25, 2000.

(51) Int. Cl.
*C12Q 1/18* (2006.01)
*C12N 5/071* (2010.01)
(52) U.S. Cl. ........................ 435/32; 435/370
(58) Field of Classification Search ........................ None
See application file for complete search history.

(56) References Cited

U.S. PATENT DOCUMENTS

| | | | |
|---|---|---|---|
| 5,290,684 A * | 3/1994 | Kelly | 435/29 |
| 5,342,777 A * | 8/1994 | Cole et al. | 435/378 |
| 5,506,131 A * | 4/1996 | Harris et al. | 435/6 |
| 5,529,920 A * | 6/1996 | Cole et al. | 435/6 |
| 5,665,589 A * | 9/1997 | Harris et al. | 435/370 |
| 5,759,765 A * | 6/1998 | Harris et al. | 435/4 |
| 6,458,589 B1 * | 10/2002 | Rambhatla et al. | 435/370 |
| 6,506,574 B1 * | 1/2003 | Rambhatla et al. | 435/21 |
| 7,015,036 B2 * | 3/2006 | Prachumsri et al. | 435/370 |
| 7,399,633 B2 * | 7/2008 | Bernstein et al. | 435/377 |
| 7,456,018 B2 * | 11/2008 | Gripon et al. | 435/370 |
| 2002/0045262 A1 * | 4/2002 | Prachumsri et al. | 435/370 |
| 2006/0160216 A1 * | 7/2006 | Prachumsri et al. | 435/370 |
| 2010/0003752 A1 * | 1/2010 | Herrera Sanchez et al. | 435/370 |

FOREIGN PATENT DOCUMENTS

WO WO 2007/084678 A2 * 7/2007

OTHER PUBLICATIONS

Stahel et al, Am. J. Trop. Med. & Hyg., 1988, 39/3:236-240 (abstract only).*
Lim et al, Toxicology in Vitro, 2007, 21:1390-1401.*
Hatabu et al, Antimicrobial Agents and Chemotherapy, Feb. 2005, 49/2:493-496.*
Mahmoudi et al, Antimicrobial Agents and Chemotherapy, Apr. 2008, 52/4:1215-1220.*
Solbach et al, Int. J. Immunopharmaco., 17/6:481-488.*
Sattabongkot et al, Am. J. Trop. Med. Hyg., May 2006, 74/5:708-715.*
Latchoumycandane et al, Toxicology and applied Pharmacology, 2006, 217:125-133.*
Fontaine et al, Life Sciences, 2000, 66/22:2193-2212.*
Sattabongkot et al. ,American Journal of Tropical Medicine and Hygiene, vol. 61, No. 3, suppl. p. 273, 1999.*
Roberts et al. ,Hepatology, vol. 19, No. 6, pp. 1390-1399, 1994.*
Davies et al. , Acta Leidensia, vol. 58, No. 2, pp. 97-114, 1989.*
Smith et al. Lancet vol. 2, No. 8405, pp. 757-758, Sep. 29, 1984.*
Kono et al, BBRC, 1996, 220:628-632.*
Walker et al (editor):The Language of Biotechnology, 1988, pp. 43 and 215 only.*
Mellouk et al, J. Immunology, 1987, 139/12:4192-4195.*
Sattabongkot J. et al., 1999. Establishment of a human hepatocyte cell line for in vitro development of *Plasmodium falciparum* liver stage. Am. J. Trop Med. Hyg. 61, p. 273.
Roberts et al., 1994. Characterization of human hepatocyte lines derived from normal liver tissue. Hepatology 19, 1390-1399.
Kono et al., 1995. Establishment of a human hepatocyte line derived from primary culture in a collagen gel sandwich culture system. Experimental Cell Res. 221, 478-485.
Miyagama et al., 1988. Effects of various factors on the growth and function of a human hepatoblastoma cell line, HuH-7—an approach for serum-free cell culture! Medline datablse accession No. NLM2484808. Official Journal of Human Cell Research Society. 4, 416-420.
Davies et al., 1989. Improved techniques for the culture of the liver stages of *Plasmodium-berghei* and their relevance to the study of causal prophylactic drugs. Acta Leidensia 58, 97-114.
Karnasuta et al., 1995. Complete development of the liver stage of *Plasmodium falciparum* in a human hepatoma cell line. Am J. Trop. Med. Hyg. 53, 607-611.
Kamboj, K. K. 1997. Current trends in research on tissue stage of malaria. Indian Journal of Medical Research 106, 120-129.
Mazier et al. 1985. Complete development of hepatic stages of *Plasmodium-falciparum* in-vitro. Science 227, 440-442.
Dessens J. et al. 2000. Identification of differentially regulated genes of *Plasmodium* by suppression subtractive hybridization. Parasitology Today 16, 354-356.

* cited by examiner

*Primary Examiner*—N. M Minnifield
(74) *Attorney, Agent, or Firm*—Elizabeth Arwine

(57) ABSTRACT

In this application is described the establishment and maintenance of a normal human hepatocyte cell line able to support complete development of malaria parasite development in vitro. The cell line can be used in methods for screening compounds affecting normal human liver cells or normal human cells infected with malaria parasites, measuring uptake of drugs or chemicals into normal human liver cells, and measuring metabolism of a drug in a normal human liver cell. Other advantages and uses of the cell line are also described.

6 Claims, 14 Drawing Sheets

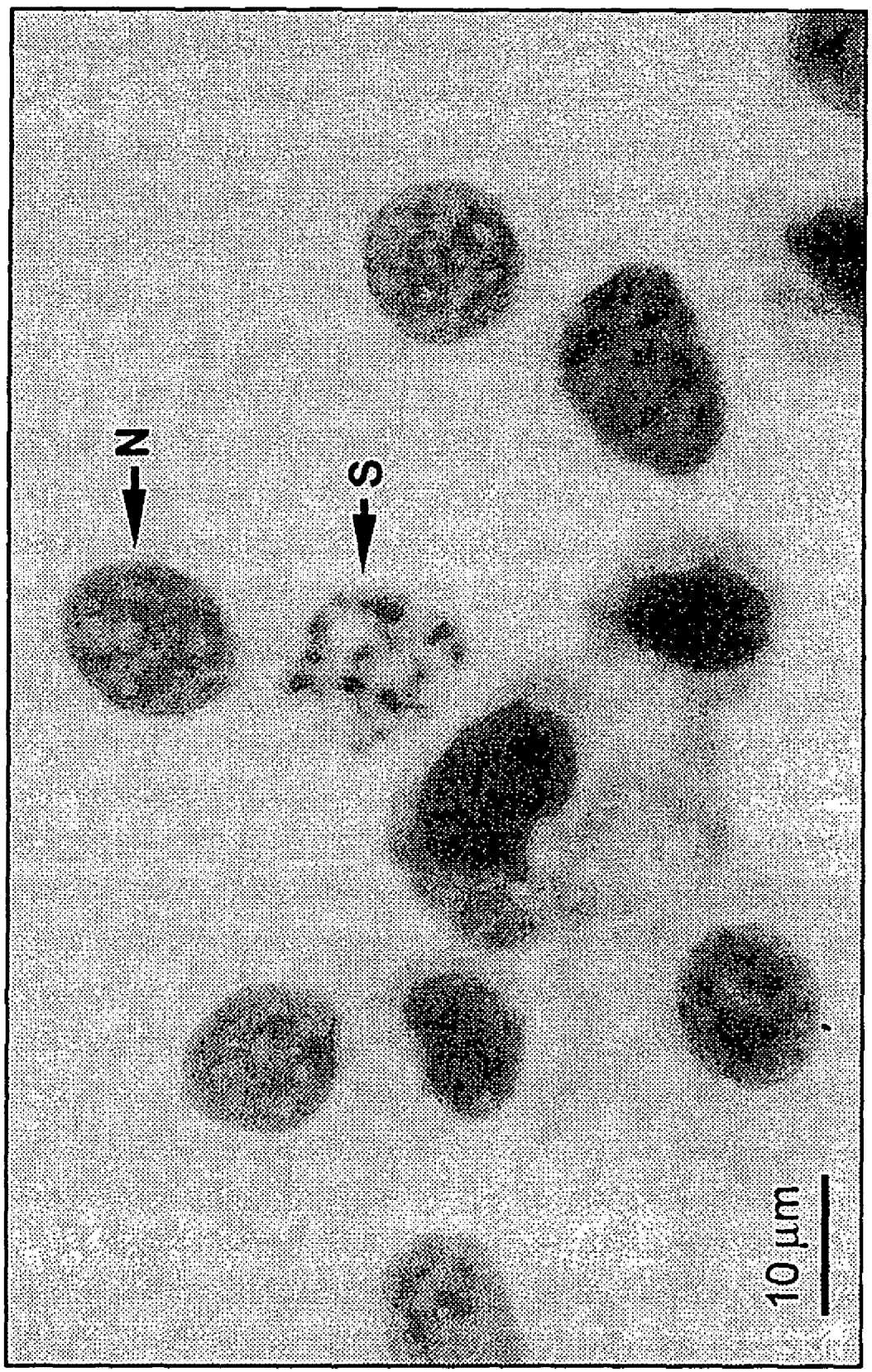

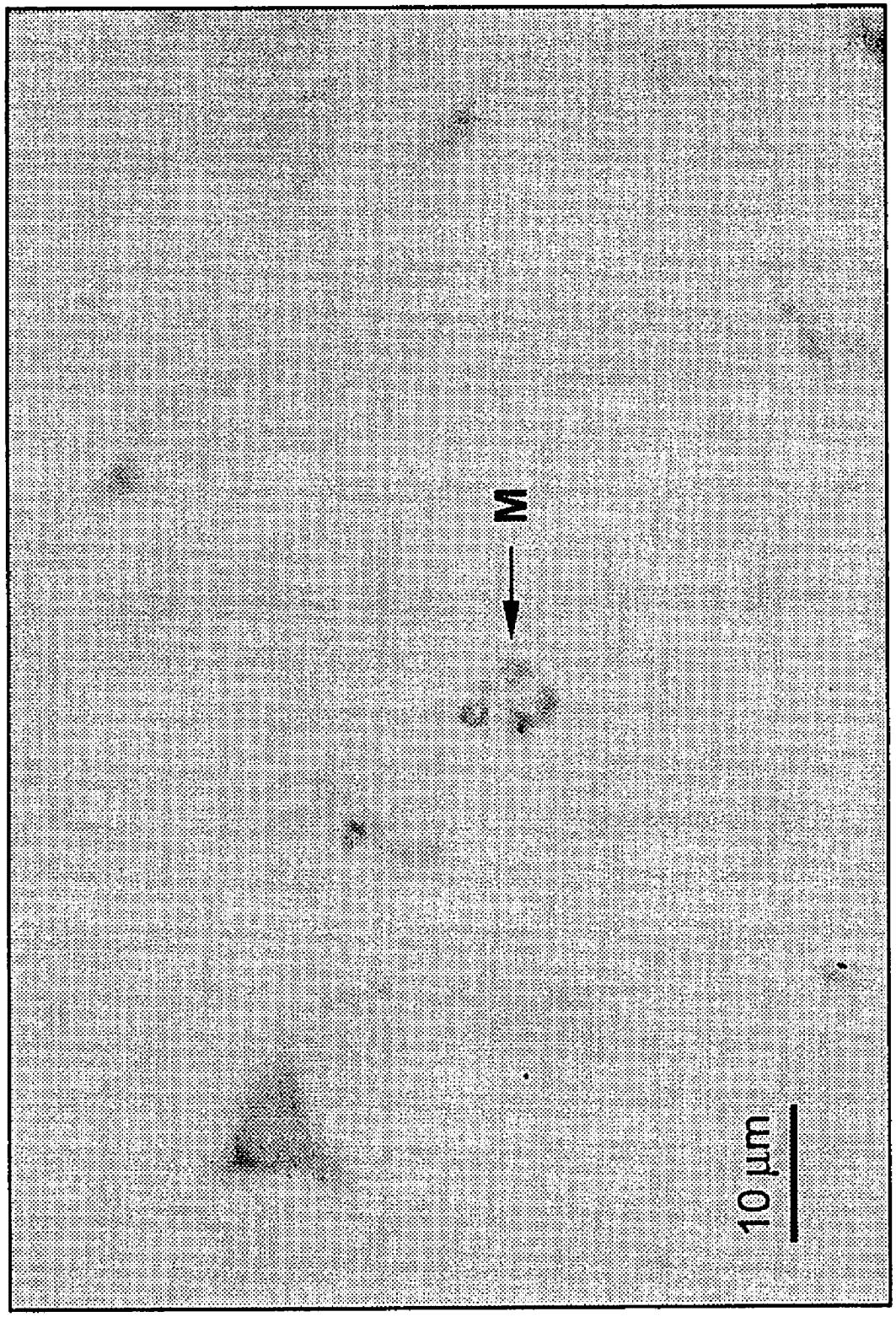

SCREENING METHODS USING NORMAL HUMAN LIVER CELL LINE

This application is a continuation-in-part of U.S. application Ser. No. 09/962,364 filed Sep. 25, 2001, now U.S. Pat. No. 7,015,036, which claims priority from U.S. Provisional Application No. 60/235,051 filed Sep. 25, 2000.

Malaria is one of the most serious health risks due to problems of multi-drug resistance and lack of an effective vaccine. Two human malaria parasites that can cause severe disease are known, *Plasmodium falciparum* (*P. falciparum*) and *Plasmodium vivax* (*P., vivax*). Development of vaccines and drugs against the disease has been difficult since the parasites can develop resistance to most of the drugs quite rapidly and the development of the parasites in the liver where is the first place for transmitting the disease to human has not been well understood. Presently, there is no efficient in vitro human liver model available to support vaccine and drug development.

Malaria sporozoites are injected into human during the blood meal of a female anopheline mosquito and rapidly invade hepatocytes. One sporozoite can develop into 20,000 merozoites, which rupture from hepatocyte, enter the bloodstream and invade erythrocytes. This initiates a cycle of intra-erythrocytic stage development, rupture and re-invasion, leading to 10-20 fold increase in the number of the parasites in the blood stream every 48 hours. These asexual erythrocytic-stage parasites are responsible for the clinical manifestations and pathology of the disease. Some erythrocytic stages differentiate into gametocytes, which are infective for mosquitoes. Fertilization occurs in the mosquito midgut, and form oocysts. Sporozoites rupture from these oocysts and invade the salivary glands of the mosquito from where they are injected into a human host. The hepatic stage of the life cycle is an ideal target for vaccine-induced protective immune responses because this stage lasts for at least 5.5 days and is not associated with pathology. Development of causal prophylaxis drug is important for protection from the disease. The animal models such as mice, monkey and in vitro culture of rat liver cells have been used for efficacy test of new drugs.

Complete development of *P. vivax* and *P. falciparum* exoerythrocytic stage was shown in primary culture of human hepatocytes (Mazier et al., 1984, Science 227, 440-442; Smith et al., 1984, Lancet 29, 757-58; Mazier et al., 1984, Nature 307, 367-69). Primary hepatocyte cultures are not feasible to use as a tool to evaluate malarial drugs and vaccines since they are expensive and their delivery schedule is uncertain. Development of *P. falciparum* exoerythrocytic stage has also been demonstrated in a human hepatoma cell line, HHS-102 (Karnasuta et al., 1995, Am. J. Trop. Med. Hyg. 53, 607-11) and *P. vivax* in HepG2-A16 (Luo et al., 1994, Chung Kuo chi Sheng Chung Hsuch Yu Chi Sheng Chung Ping Tsa Chin. 12, 8-4) but with low density of growth. In addition, these cell lines are derived from a tumorigenic cell line and would not reflect growth conditions in a normal, non-tumorigenic cell line.

Hence there is a need for a cell line established from normal liver tissue and which can support high density, complete erythrocytic development of both *P. falciparum* and *P. vivax*.

SUMMARY OF THE INVENTION

This application describes such a cell line. The cell line of the present invention, HC-04, has two important characteristics. First, the cell line was developed from normal liver tissue (hepatocytes) and second, this cell line supports in vitro development of human malaria parasites, *Plasmodium falciparum* and *Plasmodium vivax*.

Therefore, it is an object of the present invention to provide a hepatocyte cell line HC-04, the cell line deposited under the Budapest Treaty at American Type Culture Collection, Manassas, Va. on 8 Jun. 2001, assigned accession no. PTA-3441. The cell has been propagated in vitro for more than 100 passages.

It is another object of the invention to provide a method for making an immortalized human hepatocyte cell line containing cells capable of supporting *Plasmodium* exoerythrocytic growth.

It is another object of the present invention to provide a method for screening to identify compounds that affect parasite growth. In one embodiment, the method includes incubating components comprising the compound and at least one hepatocyte of the present invention which has been infected with the parasite under conditions sufficient to allow the compound and cell to interact; and determining the effect of the compound on the cell and on the parasite. A function of the parasite or cell that may be modulated (e.g., inhibited or stimulated) by the compound includes, but is not limited to, differentiation, gene expression, production of factors, response to factors. In another aspect, the present invention provides for compounds identified as inhibitory to the development or differentiation of the parasite for use as a malaria drug or vaccine for protection against malaria.

In another aspect, the invention provides a method of using the cells of the present invention to produce a certain developmental stage of the parasite. In one embodiment, a hepatocyte is cultured under conditions effective to produce a developmental stage of the parasite. By studying gene expression in the presence of a potential vaccine compound, or by producing a compound which reacts directly with an antigen on the surface of the parasite such that its growth is inhibited compounds can be identified for prophylactic or therapeutic use against malaria.

These objects and others which will become obvious to the skilled artisan are deemed to fall within the spirit and scope of the present invention and are intended to be included herein.

These and other features, aspects, and advantages of the present invention will become better understood with reference to the following description and appended claims, and accompanying drawings.

BRIEF DESCRIPTION OF THE DRAWINGS

FIG. 6. Liver merozoites (M) were found on day 28.

DETAILED DESCRIPTION

Figure 1:
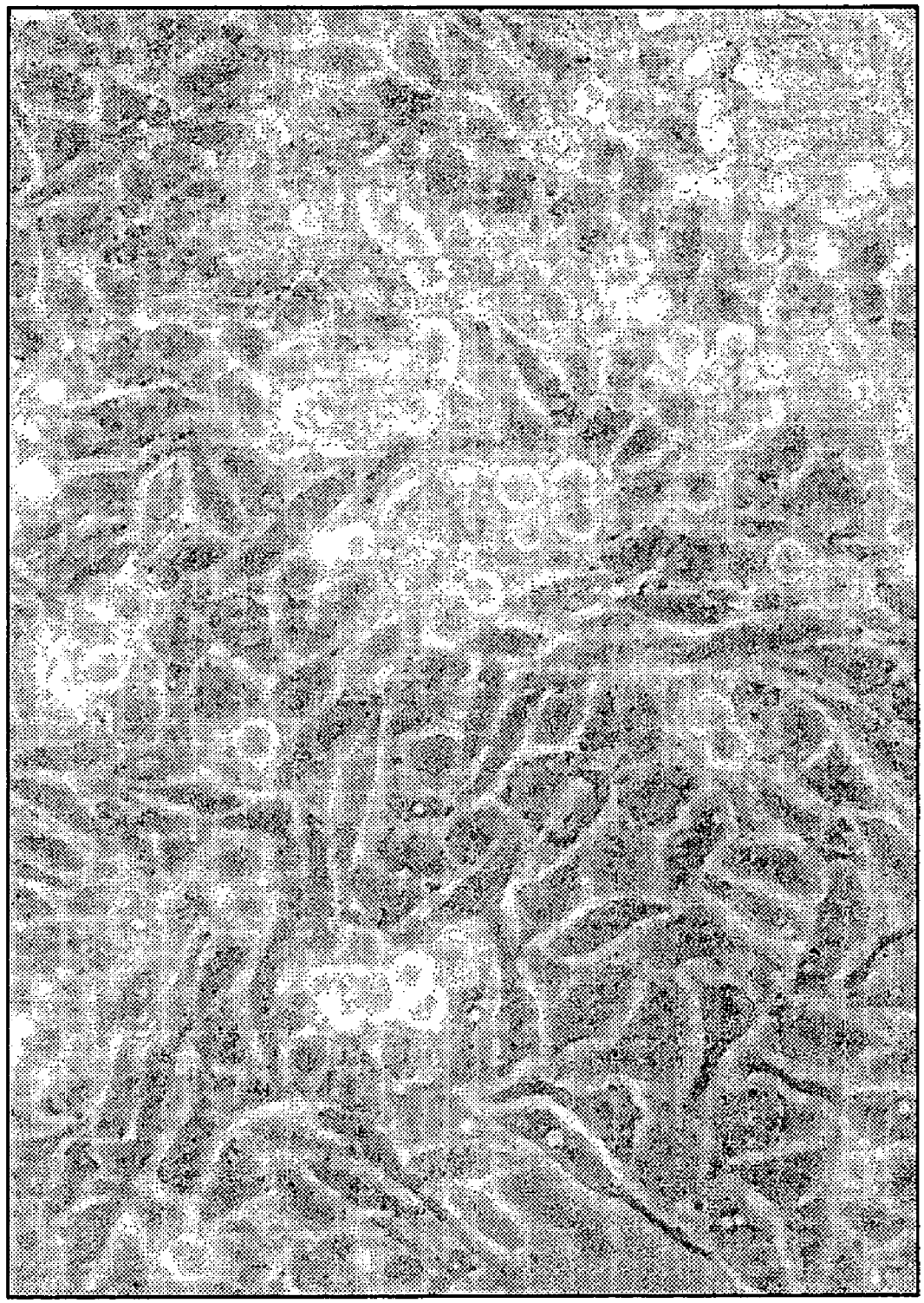
FIG. 1. Phase contrast micrograph of human hepatocytes (HC-04).

In order to provide a clearer and consistent understanding of the specification and claims, including the scope to be given such terms, the following definitions are provided.

A cell line is a population or mixture of cells of common origin growing together after several passages in vitro. By growing together in the same medium and culture conditions, the cells of the cell line share the characteristics of generally similar growth rates, temperature, gas phase, nutritional and surface requirements. The presence of cells in the cell line expressing certain substances, for example G6 Pase, can be ascertained, provided a sufficient proportion, if not all, of cells in the line are present to produce a measurable quantity of the substance. An enriched cell line is one in which cells having a certain trait, e.g. expressing G6 Pase, are present in greater proportion after one or more subculture steps, than the original cell line.

Clonal cells are those which are descended from a single cell. As a practical matter, it is difficult to obtain pure cloned cell cultures of mammalian cells. A high degree of cell purity can be obtained by successive rounds of cell enrichment. As used herein, a cell culture in which at least 90% of the cells possess a defined set of traits is termed a cloned cell culture.

Hepatocytes constitute about 80% of the cell population of the liver. They are large polygonal cells measuring between 20-30 um. Liver cells are capable of considerable regeneration when liver substance is lost to hepatotaxic processes, disease, or surgery. Hepatocytes have as many as 200-300 peroxisomes per cells which are involved in the breakdown of hydrogen peroxide produced in many of the general cytoplasmic metabolic activities. In addition, peroxisomes have specific oxidative functions in gluconeogenesis, metabolism of purines, alcohol and lipids. The smooth endoplasmic reticulum (sER) in hepatocytes contains enzymes involved in degradation and conjugation of toxins and drugs. Under conditions of hepatocyte challenge by drugs, toxins or metabolic stimulants, the sER may become the predominant organelle in the cells.

This invention is not limited to the cells, compositions, reagents, methods or uses described, as such cells, compositions, reagents, methods or uses may, of course, vary. The terminology used herein is for the purpose of describing particular embodiments only, and the terminology used herein is not intended to limit the scope of the present invention, which will only be limited by the appended claims.

All references cited herein are hereby incorporated by reference in their entirety. Nothing herein is to be construed as an admission that the invention is not entitled to antedate such disclosure by virtue of prior invention. Throughout this description, the preferred embodiment and examples shown should be considered as exemplars, rather than as limitations on the present invention.

In one embodiment, the invention provides human liver cells and a method of producing such cells. A starting material for isolating the cells can be live biopsy samples free of any pathologies evident during pathological examination.

Cells were separated from only normal portions of the liver tissue. Outer surface of the liver tissue specimen was trimmed and washed (2 times) with high concentration antibiotic-PBS buffer. The specimen was perfused by hand with cold Hepes buffer. Then the specimen was cut into small pieces and incubated in collagenase buffer at 37° C. for 30 min. After collagenase digestion, the tissue was minced and passed through 70 um nylon cell strainer (Becton Dickinson Labware). The strainer was washed and liver cells were pooled with MEM+2% FBS medium. The cell suspension was centrifuged at 800 rpm for 3 min. The pellet was washed two times with warm Hepes buffer then was resuspended in complete culture medium. The cells were assessed for viability by trypan blue exclusion and counted. The cells were plated in complete culture medium at a density of $1.3 \times 10^7$ cell per 25 $cm^2$ flask and placed in an incubator with 95% air, 5% $CO_2$ at 37° C. The culture medium was changed daily. After 47 days the cells could be trypsin digested and subcultured to new flask. The medium was changed every other day after subculturing.

When culturing liver cells, the liver biopsy are preferably delivered to the laboratory in the shortest time. Isolation of hepatocytes from liver tissue can be done by any method known in the art but preferably, the primary cell was not cultured on collagen precoated plate. The primary culture media is preferably supplemented with EGF, a growth hormone. Once established, the cells are cultured with media devoid of growth hormones and antibiotics.

Using the methods and materials described herein, a hepatocyte cell line, designated HC-04, has been derived and cultured. The cell line has been deposited at ATCC under the Budapest Treaty on 8 Jun. 2001 and has been assigned accession number PTA-3441.

The hepatocyte cell line is characterized by the presence of hyperdiploid chromosomes (2n=48-50). Abnormal chromosomes including chromosome 1p deletion, chromosome 6 derivative, triplet of chromosome 7 and chromosome 15 derivative.

Other characteristics include hepatocellular functions such as activity of G6 Pase, an enzyme that is characteristic of hepatocytes and found in very few other cell types; protein secretion such as albumin, alpha-fetoprotein and transferrin;

The invention utilizes cell culture media, growth factors, and methods for growing and maintaining cultures of hepatocytes. The cell culture media may include a growth medium that is effective to support the growth of the cells; a nutrient serum effective to support the growth of the cells; non-essential and essential amino acids, and a pyruvate salt. The growth medium can include any serum or serum-based solution that supplies nutrients effective to maintain the growth and viability of the cells. Examples of such serum include, without limitation, fetal bovine serum (FBS) and fetal calf serum (FCS). For example, the FBS may be provided in a concentration of between about 0.5% and about 25%. In particular, the FBS may be provided in a concentration of between about 1.0% and about 20%. In one embodiment, hepatocytes cells are grown in 2% FBS.

Once established, the hepatocytes can be cultured under the above-described conditioned medium using a variety of techniques.

Hepatocytes of the present invention support the development of exoerythrocytic stage of malaria-causing parasites, early liver stage, liver schizont, and liver merozoite. Sprorozoites from *P. falciparum* or *P. vivax* are added to the liver cells and after the cells are infected, human erythrocytes are added and cocultured with the liver cells. Complete development of the liver stage malaria parasite can be detected in the liver cells and early trophozoites are detected in co-cultured erythrocytes. Once the sporozoites invade the cells, they round up to form early liver stage parasites. The parasites then further develop to form liver schizonts and mature liver merozoite which rupture from the hepatocytes. When co-cultured with human red blood cells, the mature liver merozoites then invade red blood cells and develop to early blood stage parasite called trophozoites.

In another embodiment and use of the invention, hepatocytes are used to screen treatments which promote or inhibit parasite growth. High-throughput screens can be established to assess the effects of chemicals, growth factors, and drugs. A variety of components known to people conducting such test and depending on the compound to be tested can be measured to quantify the effects of the experimental treatment.

The cells are exposed to an agent or vaccine being screened prior to, along with, or after addition of sporozoite parasite stage to the cells. Several parameters can be assessed, i.e., the growth of the parasite, the effect of the parasite on the expression of certain genes in the liver cell, the development of the parasite into merozoites or other stage, the ability of the liver stage merozoites to infect red blood cells. Those substances confirmed to be inhibitory to parasite invasion or growth can also be tested in combination (e.g., combinations of two or three substances) to determine the presence of any synergistic properties among the factors.

In another embodiment, the invention provides a method for identifying a compound which modulates a parasite function in some way (e.g., modulates differentiation, parasite proliferation, production of factors or other proteins, gene expression). The method includes: a) incubating components comprising the compound and hepatocyte(s) under conditions sufficient to allow the components to interact; and b) determining the effect of the compound on the hepatocytes(s) or parasite before and after incubating in the presence of the compound. Compounds that affect parasite function include different soluble immuno-modulators eg. Cytokines or interleukins, peptides, peptidomimetics, polypeptides, chemical compounds and biologic agents. Differentiation, gene expression, cell membrane permeability, proliferation and the like can be determined by methods commonly used in the art. The term "modulation" refers to inhibition, augmentation, or stimulation of a particular parasite function.

Different culturing conditions can be applied depending on the desired objective, for example, human red cells can be co-cultured and harvested every 24-48 hr to observe mature merozoite invasion into red blood cells, or different new drug candidates can be added at different time intervals for efficacy studies, or hyperimmune sera of volunteers for vaccine study can be added for vaccine study etc. Infected liver cells can be harvested by trypsin digestion and one or more parameters can then be investigated such as gene expression in parasites or host cells, protein or enzyme expression in parasites or host cells, antigen presentation on the parasite or host cell surface after infection, or parasite development by observation of cell and parasite morphology. To study the effect of any molecules/reagent on parasite invasion, the reagent can be added before or at the same time of sporozoite inoculation. To study the effect of molecules/reagent on the development of parasites the reagents can be added at the same time or after the parasite inoculation.

After inoculation of sporozoites, the medium can be replaced with fresh medium supplemented with different concentration of drugs. Parasite development can be observed, for example, within 3 days after incubation with drug. Parasite number can be determined and compared among different drugs and drug concentrations. Parasite number can be determined by Giemsa staining, quantitative PCR, monoclonal antibody staining which recognize liver stage parasites.

The cell line of the invention can also be used as a screening model to study the effects of drug or other molecules or compounds on human liver cells. The cells of the present invention can also be used to study the metabolization of drugs. For example, drugs of interest can be added to HC04 culture or mixed with microsomes generated from HC04 cells. Metabolization of drugs can be monitored by detecting a reduction of parent compounds and/or by detecting the appearance of metabolites of said drugs.

The cell line of the invention can be used in a method for measuring uptake of drugs or other chemicals using methods known in the art. For example, cells can be incubated with radiolabeled drugs (trace amounts of [$^3$H] or [$^{14}$C]) at desired concentrations (compound specific) for various periods of time (e.g., 0, 1, 2, 3, 5, 10, 30, 60, 120 min) at 37° C., 25° C., or 4° C. (on ice). Then the cells can be washed with ice-cold PBS, lysed by ultrasonication, and the radioactivity in the lysate can be determined.

The cell line of the invention can also be used in a method for measuring qualitative and quantitative biotransformation or metabolism of drugs or other chemicals using methods known in the art. For example, cells can be incubated with different concentrations of a drug (e.g., 0, 1, 10, and 100 mM) at 37° C. If needed, specific inhibitors of drug-metabolizing enzymes can be used, and incubations can be run in the presence or absence of these inhibitors (e.g., borneol 1 mM to inhibit UGT (UDP-glucoronosyl transferase); or ketoconazole 1 mM to inhibit CYP3A4). After certain time points (e.g., 0, 10, 30, 60 min, 2 h, 6 h, 12 h, and 24 h), the cells plus culture medium can be lysed together (by ultrasonication), and the homogenate will be extracted by solvents (compound specific) and analyzed by HPLC (with compound selective methods) or LC-MS/MS.

In addition, the cell line of the invention can be used in a method for determining potential reactive metabolites of drugs or other chemicals using methods known in the art. For example, cells can be incubated with radiolabeled drugs (trace amounts of [$^3$H] or [$^{14}$C]) at 2 or 3 different concentrations (compound specific) at 37° C. After certain time points (e.g., 1 h, 4 h, 12 h, 24 h), the cells can be lysed and the proteins precipitated by trichloroacetic acid (TCA) and washed several times. The irreversible protein-bound radioactivity in the dissolved pellet is a measure of the covalently bound drug secondary to activation to a reactive metabolite. The specific covalent binding of a drug can be calculated from the specific activity of the radiolabeled drug. A threshold level of ~50 pmol/mg protein may indicate a possible risk.

The cell line of the invention can further be used in a method for assessing toxicity of chemicals or drugs using methods known in the art. For example, lactate dehydrogenase (LDH) leakage from cells into the culture medium is an established method to assess cell injury. Enzyme activity in the culture medium following exposure of cells to a chemical for a certain time will be expressed as percentage of the total of intra- and extracellular enzyme activity. Another example is the determination of cytochrome c release from mitochondria into the cytosol, which is a measure of mitochondria-mediated induction of lethal cell injury. Cells can be exposed to various concentrations of a chemical for various time points. The cells can then be harvested, homogenized, and mitochondria and cytosol isolated by differential centrifugation. The subcellular fractions can then be lysed, loaded onto SDS-PAGE gels, and probed with a specific antibody against cytochrome c.

In another embodiment, the cell line of the present invention can be used in a method for measuring drug-drug interactions using methods known in the art. For example, a standard concentration of drug A (compound specific) can be incubated together with various concentrations of drug B with HC-04 cells. The cells plus supernatants can be harvested, and the decrease in concentrations of drug A (or the time dependent increase in metabolites of drug A) will be determined by HPLC or LS-MS/MS. The extent to which drug B can inhibit the metabolism of drug A may be calculated. Two types of incubations may be run; first, the two drugs can be added to the cells concomitantly (standard incubation). Alternatively, drug B (the potential inhibitor) can be added alone 15 min prior to the addition of drug A. If the inhibition under these latter conditions is higher than under the former conditions, then it is likely that the inhibition is irreversible ("mechanism-based").

Any drug can be tested on HC-04 cells (i.e., drugs on the market, or drugs in clinical trials). Also, drug candidates (chemicals that are in preclinical phases of testing and that are potential drugs) can be tested. In addition, drugs that have been on the market and that have been withdrawn due to toxicity, or drugs whose further development has been discontinued, can be used. Finally, any other chemical can be tested (e.g., environmental chemicals that are relevant for human exposure). This includes novel compounds with an unknown toxicity profile, or old chemicals with a well-known cellular toxicity profile.

In another embodiment of the invention, hepatocytes or their infected derivatives can be used for in vitro tests and biosensors. These can replace various animal models, and form novel human based tests.

Incubating includes conditions which allow contact between the test compound and the parasite or parasite infected cell. For example, it may be desirable to test an array of compounds or small molecules on a single or few hepatocytes or parasite-infected hepatocytes on a "chip" or other solid support.

The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., Bio/Technology, 3:1008-1012, 1985), allele-specific oligonucleotide (ASO) probe analysis (Conner et al., Proc. Natl. Acad. Sci. USA, 80:278, 1983), oligonucleotide ligation assays (OLAs) (Landegren et al., Science, 241:1077, 1988), and the like. Molecular techniques for DNA analysis have been reviewed (Landegren et al., Science, 242:229-237, 1988).

In another aspect, cells cultured or modified using the materials and methods provided by the present invention are mounted to support surfaces to screen for bioactive substances. In one example, the cells are coupled with a substrate such that electrophysiological changes in the cells or the parasite in response to external stimuli can be measured, e.g., for use as a high-throughput screen for bioactive substances. The cells can be transfected with DNA that targets, expresses, or knocks-out specific genes or gene products in the cell. By providing such chip-mounted cells coupled with measuring devices, such as a computer, many compounds can be screened rapidly and accurately. The biosensor could also be coupled to the measuring device in arrays for large-scale parallel screening.

In another use of the invention, hepatocytes or their infected derivatives can be used as in vitro models for malaria. The effect(s) of manipulation, for example, the parasite genome can be altered and then tested for higher sensitivity to a chemical, or inability to infect a cell. These cells will be especially useful for the study of malaria, where large-scale or serial manipulations are required such as sequential administration of different therapeutic or prophylactic drugs or compounds.

In one aspect, the methods and culture media of the present invention are used to produce hepatocytes having multiple genetic modifications. Multiple genetic alteration of cells is desirable for many reasons, such as providing modified cells for gene therapy and replacement tissues for grafting or implantation (e.g., to avoid host rejection of the cells). This application can be used to model or treat contiguous gene disorders, aneuploidy or other large-scale chromosomal phenomenon.

In another embodiment and use of the invention, multiple changes are made to the cell genome using the above mentioned techniques. Serial transgenic events using different drug selection genes in each construct, followed by appropriate drug selection of the cells, can be used to accomplish this.

Genetic constructs are introduced into cells by electroporation, calcium phosphate, microinjection, lipofection, retroviral or other viral or microbial vector or other means. By design, the constructs are not integrated into the genome or stably propagated as an episome. These constructs have a transient effect on cells. Alternatively, the constructs are allowed to incorporate stably into the genome.

For example, hepatocytes are grown using the culture media and methods described herein. A first gene in at least one of the cells of the cell culture is modified and from the resulting culture a first clone population of modified cells is derived. The first clone population is grown in the culture media of the invention and a second gene in at least one cell of the first clone population is modified to produce a second clone population having modified the first and second genes.

The methods used to perform the genetic modifications to the cells can be any of those known in the molecular biological arts for making genetic alternations. Such methods include, but are not limited to, the use of positive-negative selector vectors, yeast artificial chromosomes (YACs), and others known to persons in the art.

In another use of the invention, hepatocytes or their derivatives are used to repair or supplement damaged tissues or organs. Removal of cell-surface molecules responsible for transplantation rejection in order to generate universal donor cells. Deletion of the Class II MHC genes (Cosgrove et al., Cell, 66:1051-1066, 1991) improves the outcome of transplantation. As an alternative to a universal donor approach to histocompatibility, genetic manipulation could be used to generate "custom" MHC profiles to match individual need. The present invention encompasses all such modifications that reduce or eliminate organ graft rejection when employing cells, cell lines (or any parts or derivatives thereof) derived from the hepatocytes of the present invention. These molecules, termed HLA antigens in humans, comprise MHC class I and II membrane glycoproteins. For non-hematopoietic cells and tissues, elimination or reduction of MHC class I molecules is accomplished by targeted knockout of the human $\beta_2$-microglobulin gene, as has been accomplished with mouse ES cells (Zijlstra et al, Nature 342:435-438, 1989). Non-hematopoietic cells do not normally produce MHC class II molecules. For hematopoietic cells, the presence of MEC class II glycoproteins may be reduced or eliminated by targeted knockout of the HLA-DP, -DQ, and -DR loci, which are analogous to knockouts of the E and A loci in mouse ES cells (Cosgrove et al, Cell 66:1051-1066, 1991).

In another use of the invention hepatocytes or their derivatives can be used for transplantation to non-human animals. If desired, such cells may be genetically modified for purposes of gene therapy.

In another use of the invention, hepatocytes or their derivatives can be used as a source of genetic material such as nuclei, genomic DNA, chromosomes, genes, RNA, and cDNAs. These materials can be used to construct libraries and screening arrays used to discover markers of liver cells.

In another use of the invention, hepatocytes or their derivatives can be used as a source of cells to develop antibodies useful in the study of human liver or malaria infected hepatocytes. Intact wild type, genetically altered, physically or biochemically altered, or parasite infected cells or their membrane extracts can be used as immuogen for the formation of mono- or polyclonal antibodies to cell surface molecules.

Another use of hepatocytes is in the biosynthetic production of macromolecules. Non-limiting examples of products that could be produced are proteins, hormones, growth factors, cytokines, enzymes, receptors, binding proteins, signal transduction molecules, cell surface antigens, and structural molecules. Biosynthetic products can be secreted into the growth media or produced intracellularly or contained within the cell membrane, and harvested after cell disruption. Genetic modification of the gene coding for the macromolecule to be biosynthetically produced can be used to alter its characteristics in order to supplement or enhance functionality. In this way, novel enhanced-property macromolecules can be created.

Additionally, the hepatocytes or cell lines of the invention are a source of RNA for the construction of hepatocyte cDNA libraries. Gene expression during infection with the parasite has traditionally been difficult to study due to the scarcity of pertinent nucleic acid, molecules, cells and tissues. Using the techniques of the present invention, one of ordinary skill in the art can overcome these difficulties by generating specific nucleic acid, molecules, cells, tissues and genetic material.

Pharmaceuticals, diagnostics, or antibodies, used in manufacturing or processing, are also produced using cells of the present invention. Exogenous foreign or homologous DNA is transferred to hepatocytes by electroporation, calcium phosphate, microinjection, lipofection, retro- or other viral or microbial vector or other means. The hepatocytes are screened for incorporation of this DNA, or are used in nuclear transfer systems. These proteins or other molecules are harvested from resulting cell cultures for further purification. For example, human blood clotting factors VIII and IX may be produced for treatment of hemophilia.

Non-limiting examples of the following pharmaceutical, therapeutic, processing, manufacturing or compositional proteins that may be produced in this manner include: blood proteins (clotting factors VIII and IX, complement factors or components, hemoglobins or other blood proteins and the like); hormones (insulin, growth hormone, thyroid hormone, gonadotrophins, PMSG, trophic hormones, prolactin, oxytocin, dopamine, catecholamines and the like); growth factors (EGF, PDGF, NGF, IGF and the like); cytokines (interleukins, CSF, GMCSF, TNF, TGF.alpha., TGF.beta., and the like); enzymes (tissue plasminogen activator, streptokinase, cholesterol biosynthetic or degradative, digestive, steroidogenic, kinases, phosphodiesterases, methylases, demethylases, dehydrogenases, cellulases, proteases, lipases, phospholipases, aromatase, cytochromes adenylate or guanylate cyclases and the like); hormone or other receptors (LDL, HDL, steroid, protein, peptide, lipid or prostaglandin and the like); binding proteins (steroid binding proteins, growth hormone or growth factor binding proteins and the like); immune system proteins (antibodies, SLA or MHC gene products); antigens (bacterial, parasitic, viral, allergens, and the like); translation or transcription factors, oncoproteins or proto-oncoproteins.

The nucleotide sequence of the transgene may encode a precursor form of the protein ultimately harvested from the transgenic or transformed cells or cell cultures of the present invention. Preferably, expression of the transgene is inducible. Alternatively, cells may be screened by techniques well known to those of ordinary skill in the art to determine the expression of the transgene by using it as a probe for testing mRNA from cell lines.

Production of differentiated cells for replacement, repair or augmentation of damaged, nonfunctional, or impaired cells or tissues are another use provided by the present invention. Exogenous foreign or homologous DNA may be transferred to hepatocytes by electroporation, calcium phosphate, microinjection, lipofection, retro- or other viral or microbial vector or other means. The cells are screened for incorporation for this DNA or used in nuclear transfer systems. These cells and/or tissues are harvested from cell cultures, or resulting cell lines for use in repairing or augmenting a defect. For example, cells, cell products, tissues or the products of cell cultures may be used in treating subjects having liver disease.

The following examples are intended to illustrate but not limit the invention.

EXAMPLE 1

Establishment of Human Hepatocyte Line (HC-04)

Source of liver cells: liver biopsy sample was provided by the Department of Surgery, Faculty of Medicine, Ramathibodi Hospital, Mahidol University, Bangkok, Thailand. The Department of Surgery at Ramathibodi Hospital routinely collects a liver biopsy sample and removes a portion of the liver when a patient has liver disease. The liver tissue was normally sent to the laboratory for pathological examination of the tissue. Excess liver tissue that was not used in the pathological examination was donated to AFRMS.

The method of liver cell preparation and culture was modified from Roberts et al, 1994, Hepatology 19, 1390-1399 and Kono et al., 1995, Experimental Cell Research 221, 478-485. Screening for development of exoerythrocytic stage of human malaria was modified from Karnasuta et al., 1995, Am. J. Trop. Med. Hyg. 53, 607-11.

Liver tissue was aseptically kept at 4° C. in transporting medium (30 ml 1×RPMI 1640, 25 mg gentamycin, 10,000 Unit penicillin, 10 mg streptomycin, 25 ug amphotericinB) before being delivered to AFRIMS. All media and buffers used for processing of liver cells were warm at 37° C. except perfusion and washing buffer were kept cold. After receiving the tissue all processes were done in biological safety hood. HC-04 was processed from the fourth liver tissue received from the hospital. Cells were separated from only normal portion of liver tissue. Outer surface of the liver tissue specimen was trimmed and washed (2 times) with high concentration antibiotic-PBS buffer. The specimen was perfused by hand with cold Hepes buffer (2.38 g Hepes, 8 g NaCl, 0.2 g KCl, 0.1 g $NaHPO_4$, 1.8 g glucose, 0.2 g EGTA, 1,000 ml DW). Then the specimen was cut into small pieces and incubated in collagenase buffer (0.05 g Collagenase type IV, 0.07 g $CaCl_2$, 100 ml Hepes buffer) at 37° C. for 30 min. After collagenase digestion, the tissue was minced and passed through 70 um nylon cell strainer (Becton Dickinson Labware). The strainer was washed and liver cells were pooled with MEM+2% FBS medium. The cell suspension was centrifuged at 800 rpm (Sorvall, model RT 6000B) for 3 min. The pellet was washed two times with warm Hepes buffer then was resuspended in complete culture medium (45 ml 1×MEM, 45 ml 1×F12, 100 ug insulin, 0.36 mg hydrocortisone, 0.5 mg linoleic acid, 12 mg nicotinamide, 0.36 mg thyrotropin releasing factor (TRF), 1 ug L-EGF, 3.48 mg glucagon, 0.129 mg selenous acid, 100 ul dimethylsulfoxide (DMSO), 10 ml FBS, 1 ml 20 mM L-Glu, 1 ml 100×MEM essential amino acid, 1 ml 100× pyruvic acid). The cells were assessed for viability by trypan blue exclusion and counted. The cells were plated in complete culture medium at a density of $1.3 \times 10^7$ cell per 25 $cm_2$ flask and placed in an incubator with 95% air 5% $CO_2$ at 37° C. The culture medium was changed daily. After 47 days the cells could be trypsin digested (12 ml 2.5% trypsin in $H_2O$, 10 ml 10× trypsin diluent, 5 ml 20×EDTA, 90 ml $H_2O$; 10× trypsin diluent=1 g KCl, 0.15 g KHPO4, 0.96 g $NaHCO_3$, 0.15 g $NaHPO_4$, 2 g NaCl, 2.5 g Dextrose, 250 ml $H_2O$) and subcultured to new flask. The medium was changed every other day after subculturing. HC-04 cells have continued to proliferate within this laboratory for more than 2 years. The cells have been trypsin digested and passed to grow in new containers for more than 100 passages. HC-04 cells are able to proliferate after being frozen and thawed.

EXAMPLE 2

Development of Exoerythrocytic Stage Malaria

The liver cells (HC-04) were plated into 96-well tissue culture plates and maintained in complete culture medium supplemented with antibiotics and fetal bovine serum until confluent at 37° C. in an incubator with 95% air 5% CO2. *Anopheles dirus* (Bangkok colony) mosquitoes were infected by membrane feeding using cultured *P. falciparum* gametocytes from a Thai isolate or *Plasmodium vivax* infected blood from patients. Malaria parasites (sporozoites) were harvested from salivary gland of malaria infected mosquitoes. Sporozoites were harvested three weeks post-feeding using semi-sterile techniques. Sporozoites were prepared in culture medium supplement with antibiotics. The sporozoites were added to the liver cells previously cultured for 24-48 hours. Malaria sporozoites are added to confluent cells at 1:1 ratio. Medium was changed 4 hr after sporozoite inoculation and every 48 hr. Development of liver-stage parasite was examined on days 4, 7, 10, 14, 21, and 28 after sporozoite inoculation. The liver cells were harvested and spread on surface of glass slides using cytospin centrifugation. To determine whether the development of liver stage parasites could be completed in HC-04 cells, human erythrocytes were added and co-cultured with the cells. The human erythrocytes were harvested and smear on slides on days 4, 7, 10, 14, 21, and 28 after sporozoite inoculation. The liver cell and human erythrocyte slides were stained with Giemsa. Some of the liver cell slides were selected and parasite development was confirmed by immunofluorescent staining with serum from malaria patients and anti-circumsporozoite protein monoclonal antibodies. Complete development of *P. falciparum* and *P. vivax* liver stages were observed in HC-04 cells. Early trophozoites of *P. falciparum* and *P. vivax* were observed in human erythrocytes co-cultured with liver cells. Photographs of parasite development in liver cells and in human erythrocytes are presented in FIGS. 3-7.

EXAMPLE 3

Characterization of Hepatocyte Cell Line

Figure 2:
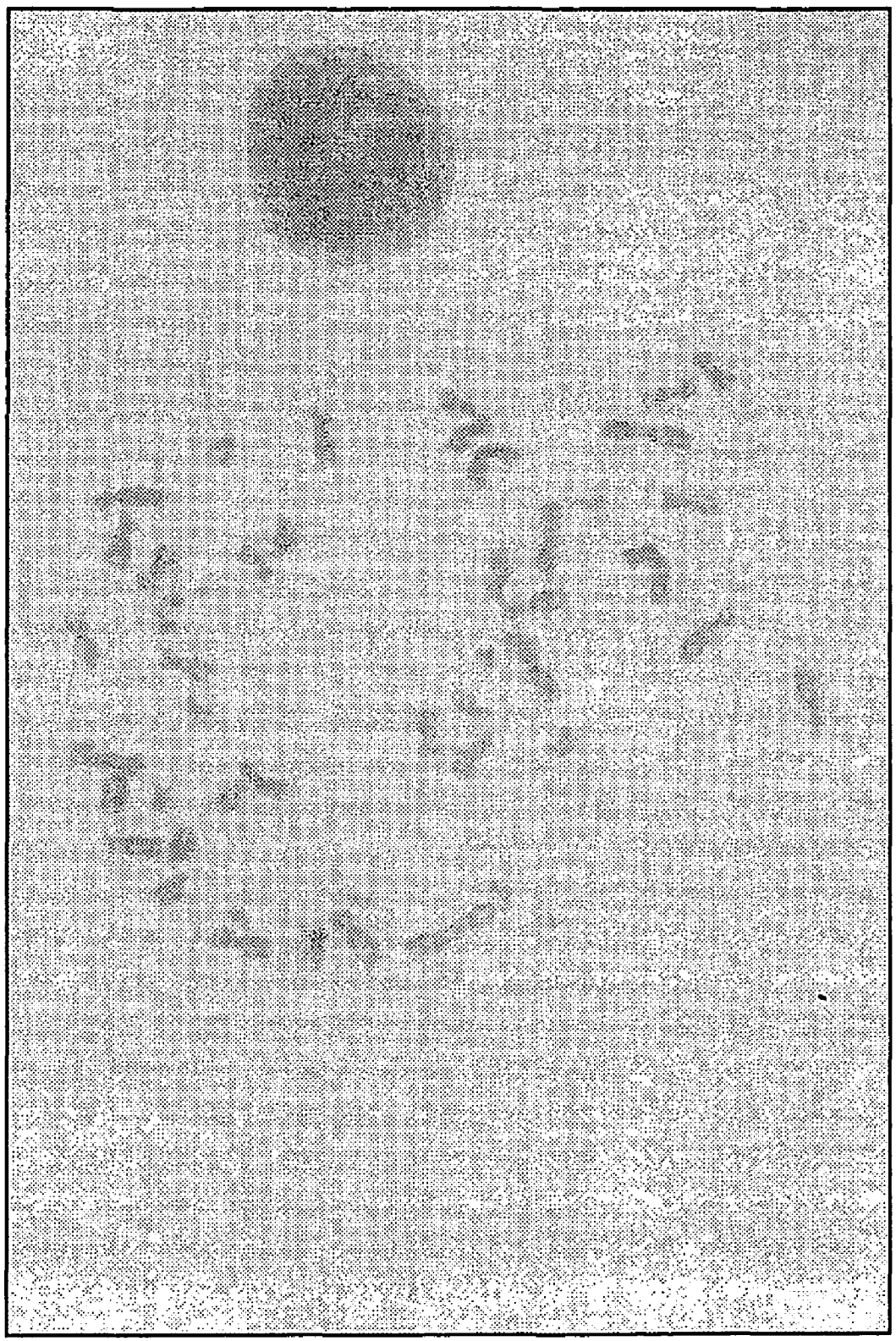
FIG. 2. Chromosomes of HC04 prepared from cell culture passage #6.
Figure 3A:
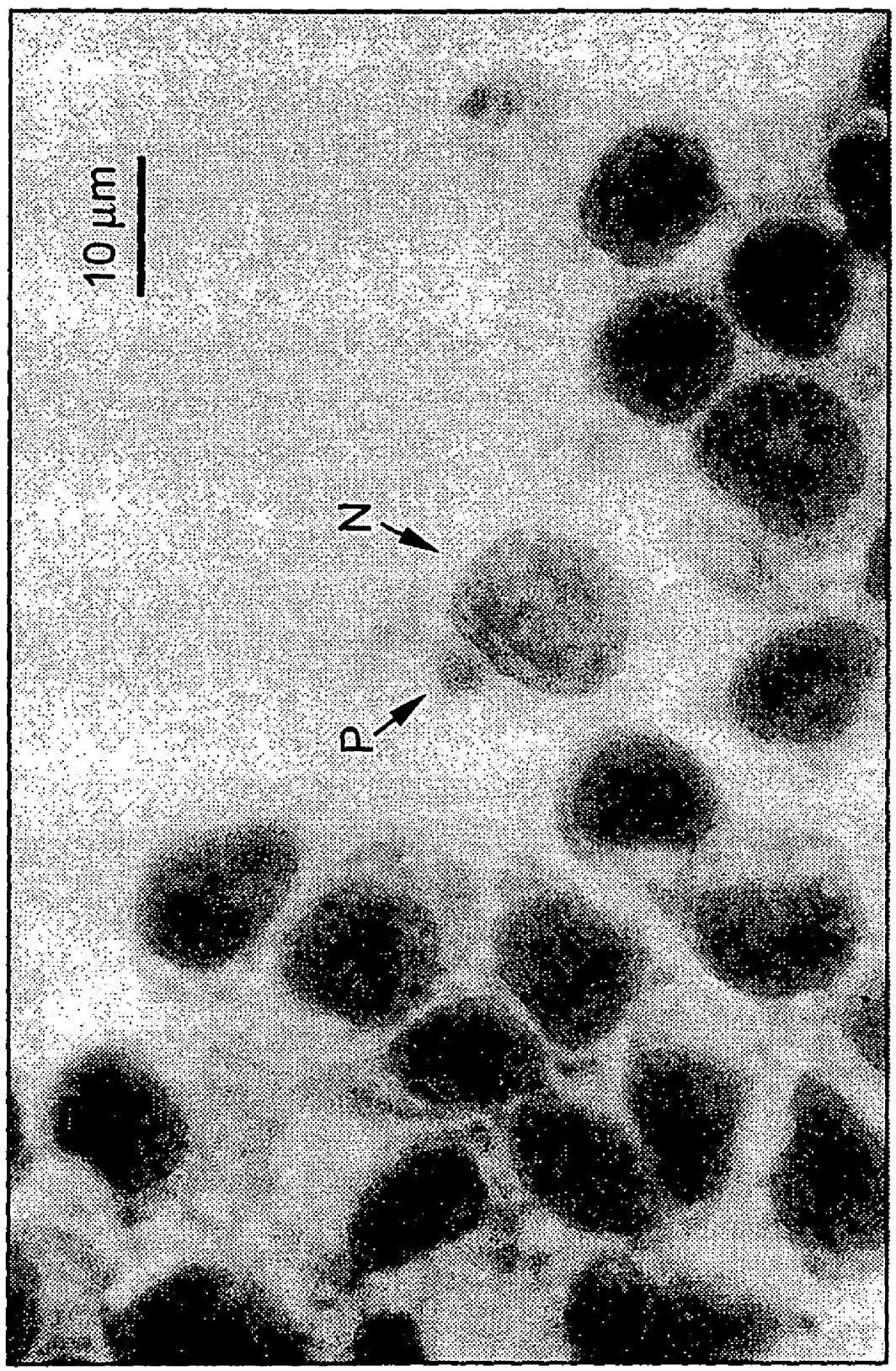
FIG. 3. Early exoerythrocytic parasites (P) were found in cytoplasm of liver cells (N=nucleus of liver cell) 3A. Giemsa staining. 3B. IFA staining with human antibody and mouse monoclonal antibody. The antibodies bind to surface of parasite. Liver cells were counterstained with Evan blue. 3C. The same slides as 2B after being washed and stained with Giemsa.
Figure 3B:
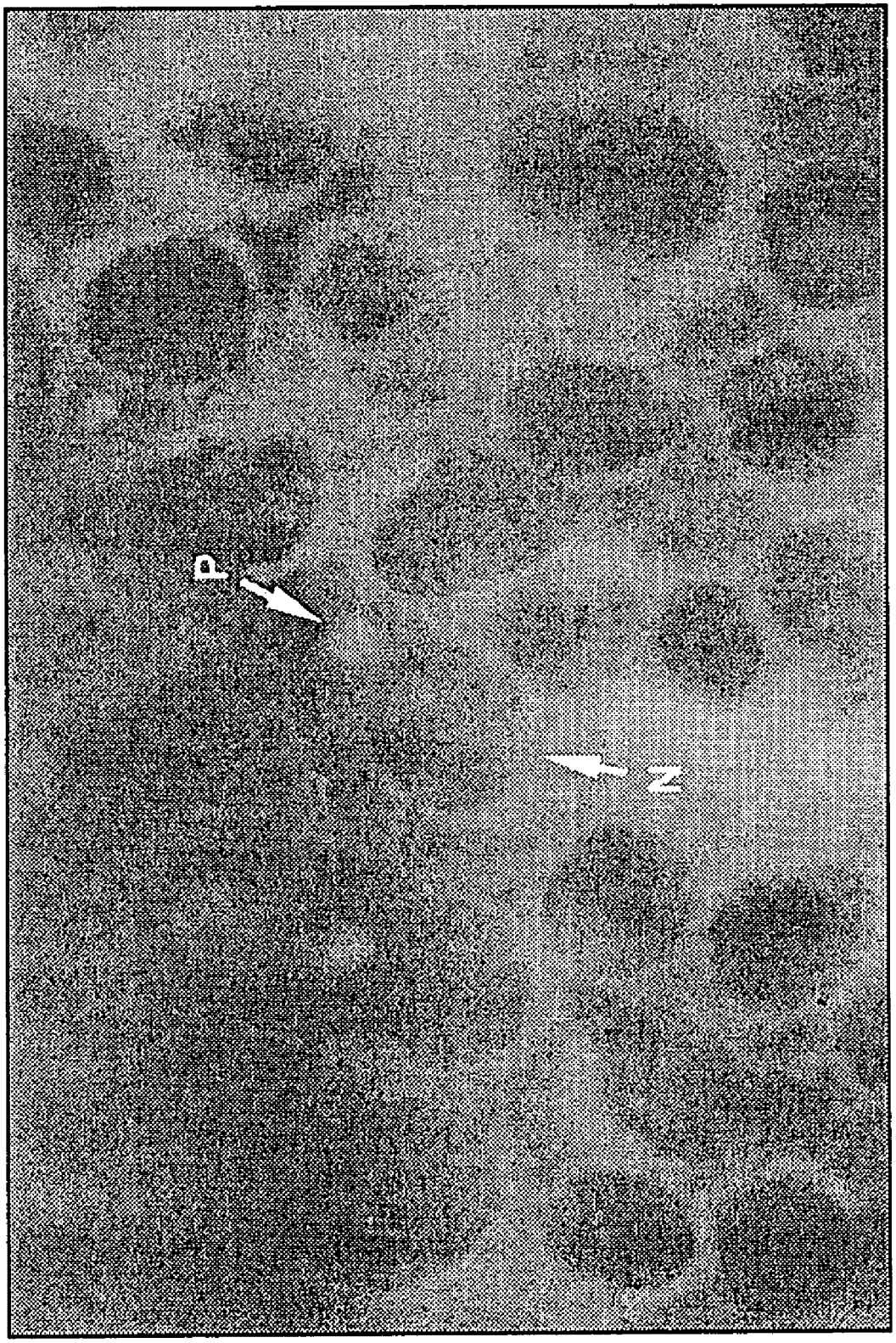
Figure 3C:
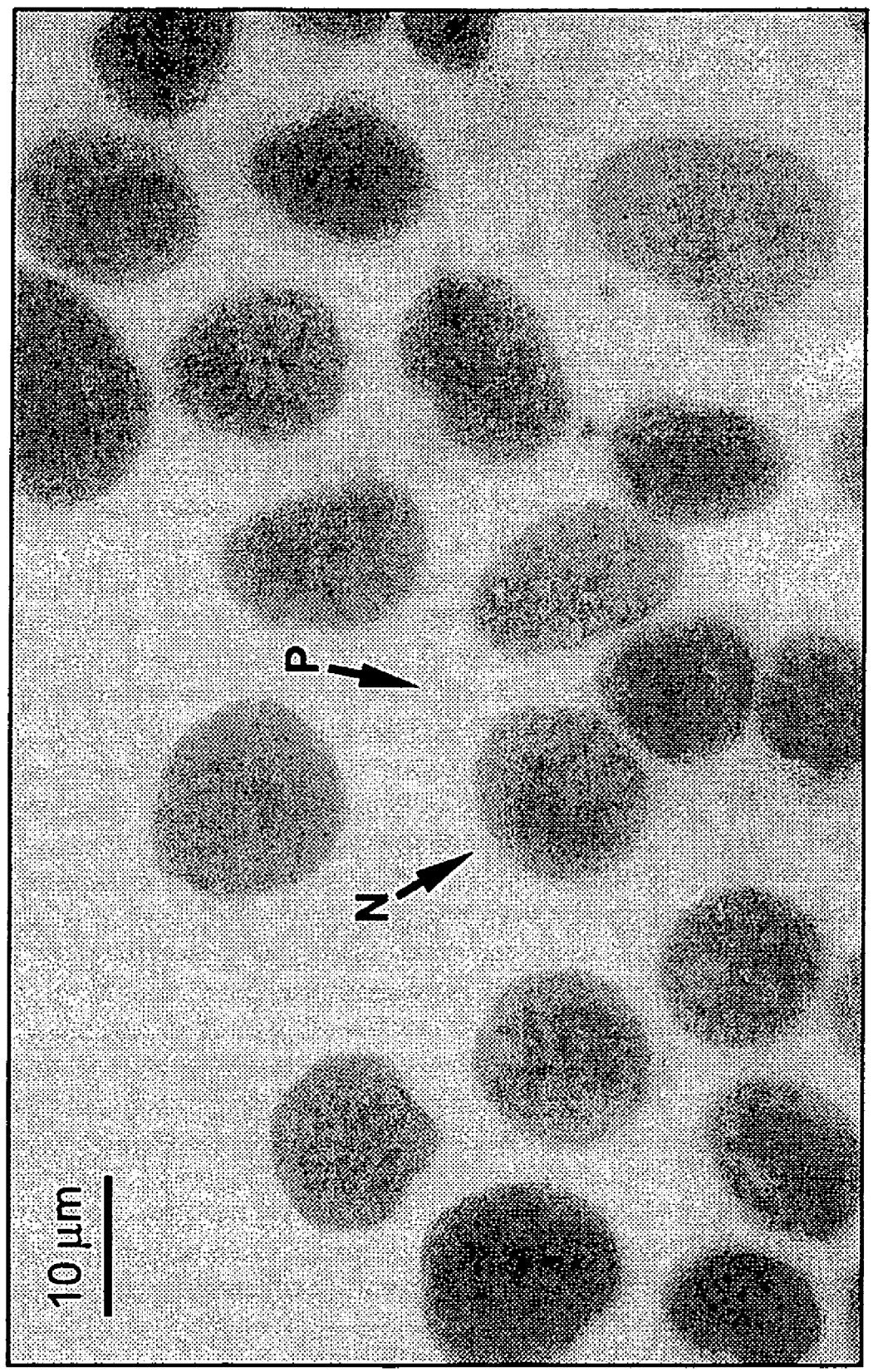
Figure 4A:
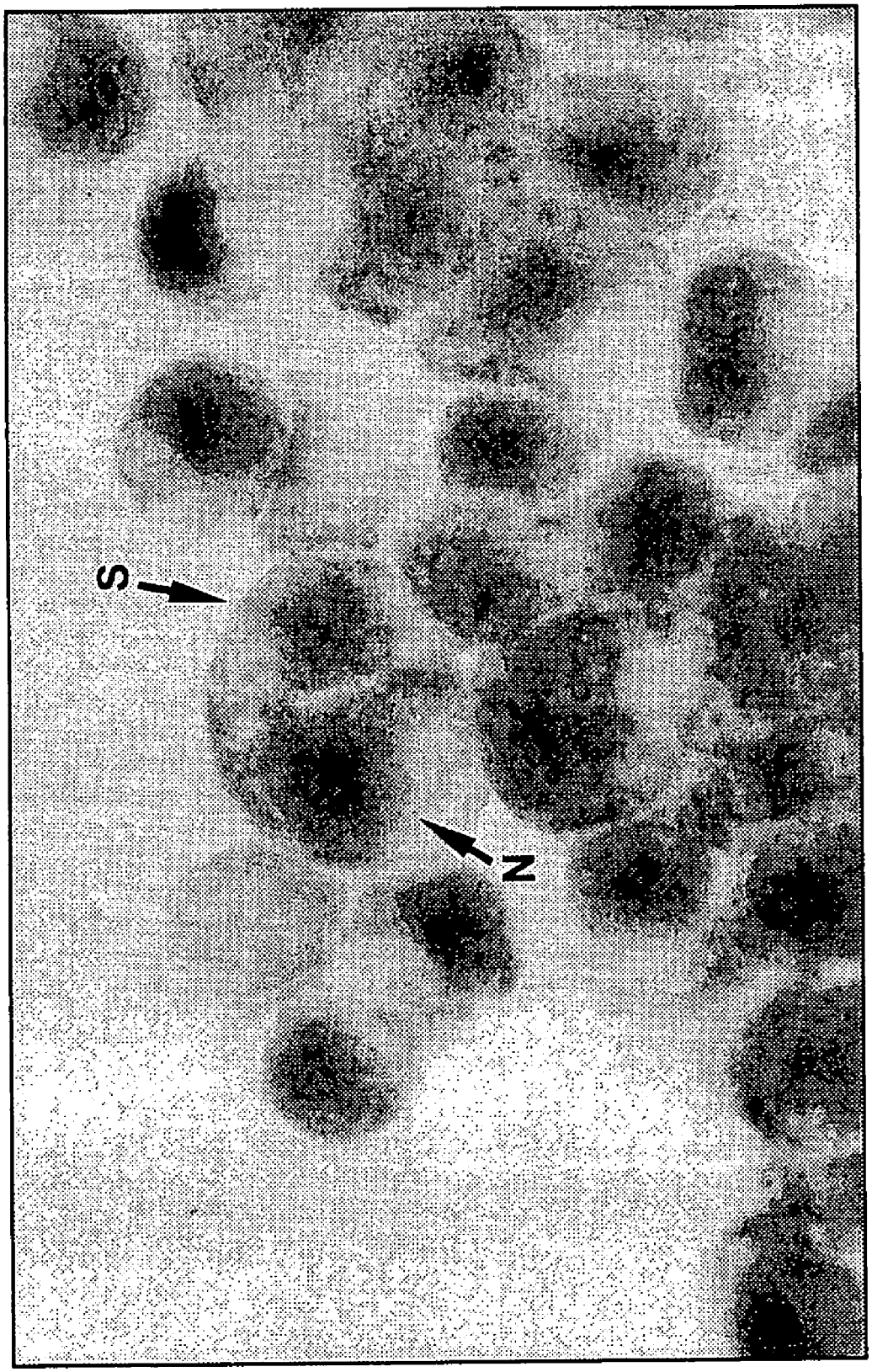
FIG. 4. Liver schizonts (S) were observed from day 7 to day 28. (4A) 7 days schizont. (4B) 21 days schizont. (4C) 28 days schizont.
Figure 4B:
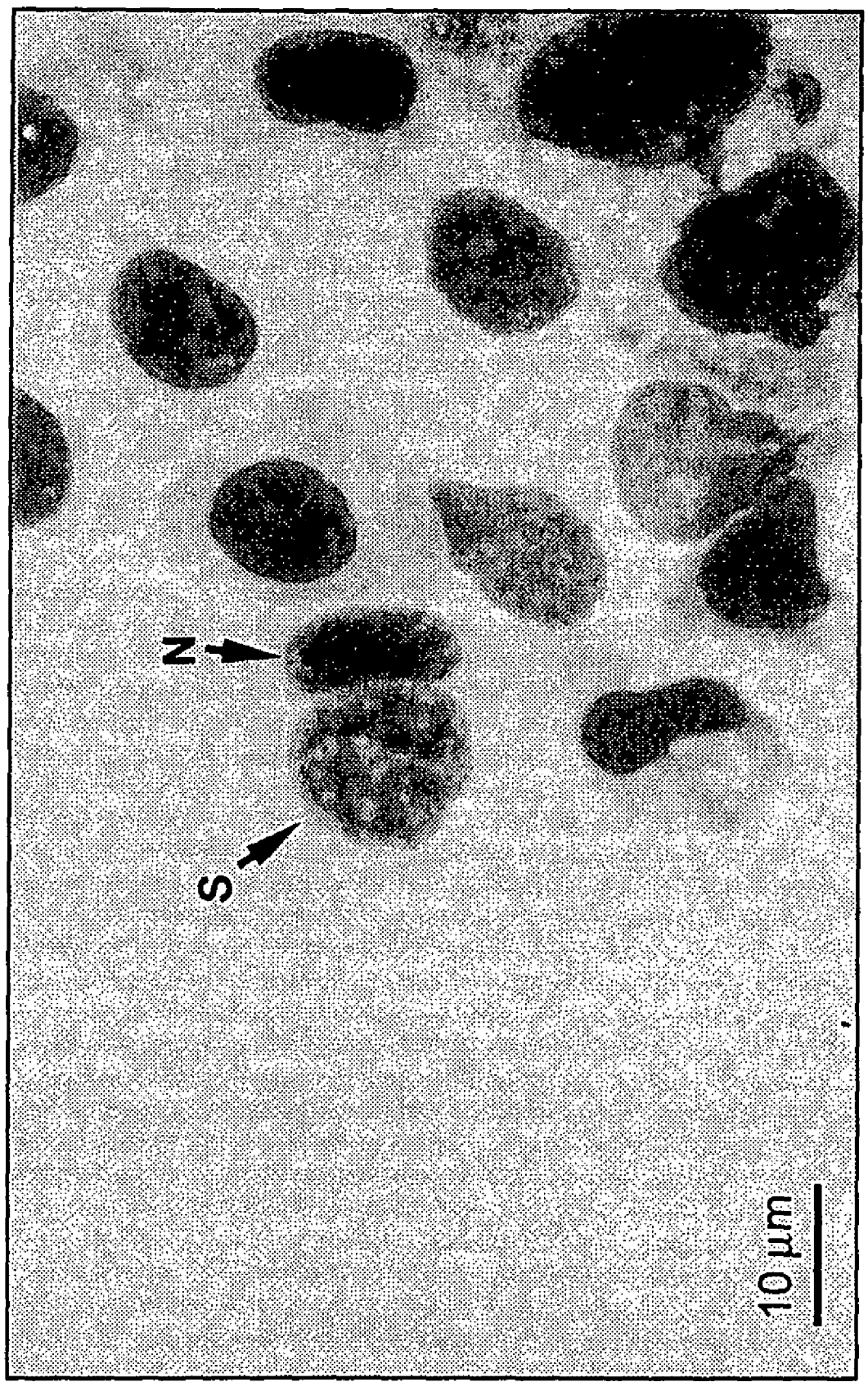
Figure 5A:
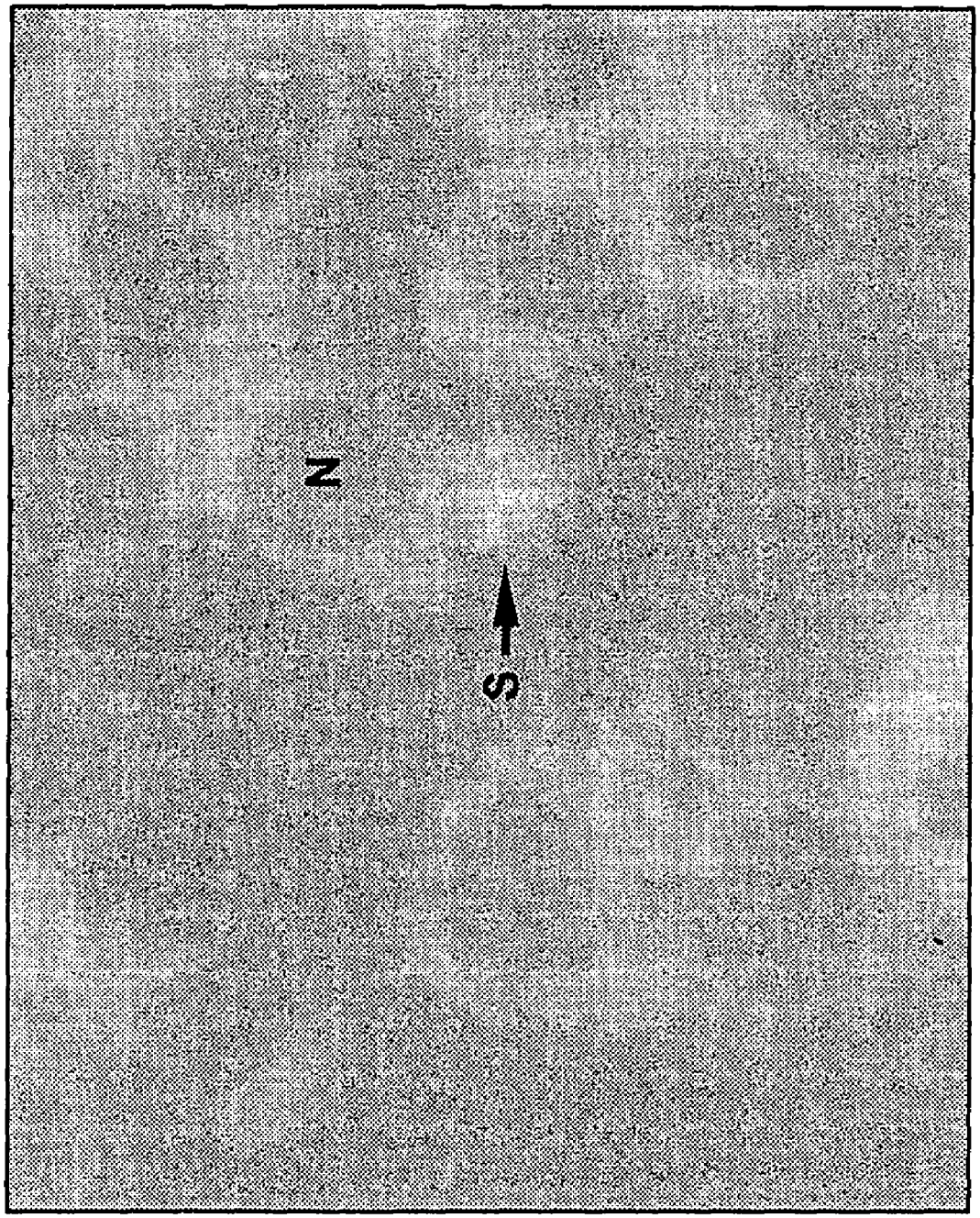
FIG. 5. Schizont (S) were observed on day 14 with (5A) IFA staining with human antibody and MAB and compared with (5B) Giemsa staining of the same specimen.
Figure 5B:
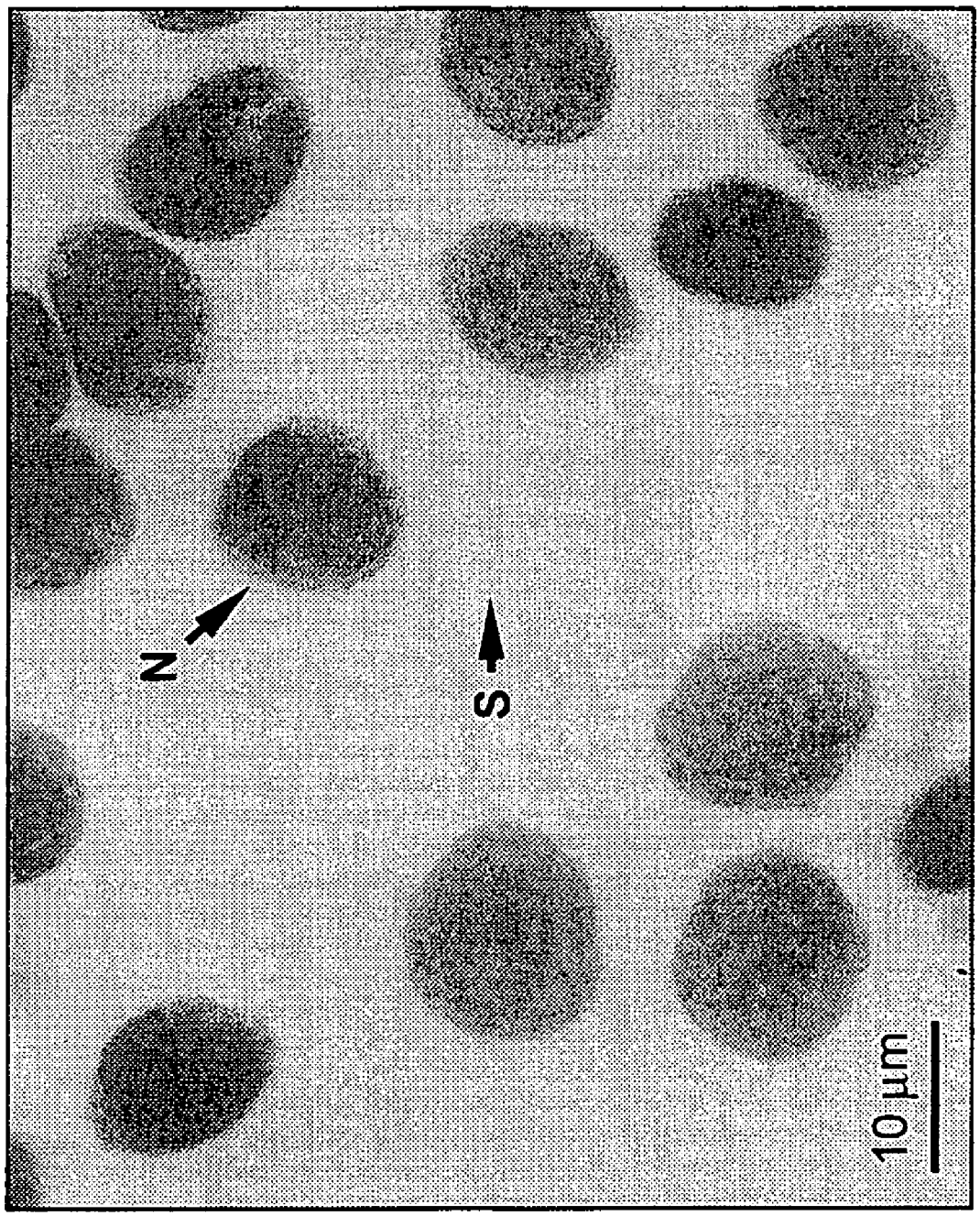

Human chromosomes from different passages of HC-04 cells were studied. The major characters from cells prepared from different passages were similar. These cells are all in the hyperdiploid range (2n=48-50) (See FIG. 2).ABnormal chromosomes including chromosome 1p deletion, chromosome 6 derivative, triplet of chromosome 7 and chromosome 15 derivative.

Hepatocellular functions such as G6 Pase activity, protein secretion such as albumin, alpha-fetoprotein and transferrin, and function of cytochromes P450 2A1 (Roberts et al., 1994, supra) were identified in this cell line. None of the receptors of hepatitis B, hepatitis A and hepatitis E virus were found on the cell surface. MHC class I, MHC class II, and IFN-gamma receptor were presented on HC-04 cell surface.

One of the critical issues in a potential application for pharmacological/toxicological research is whether these cells stably express a number of transmembrane transporters, drug-metabolizing enzymes, and the transcription factors that regulate these transporters and enzymes. This is important as many cell lines dedifferentiate and lose the ability to express many genes that are not essential for cell growth and proliferation. Hepatocyte-selective gene expression was determined both at the mRNA (transcript) and the protein level. A summary of transcript expression of HC04 cells (as assessed by RT-PCR) is given in Table 1. In particular, the major cytochrome P450, CYP3A4/5, is expressed at relatively high levels. Most importantly, PXR, the transcription factor regulating CYP3A4/5 and other genes, is also expressed in HC04. Furthermore, a number of critical phase II enzymes (UGT, SULT, and GST-A) are also expressed. In addition, the major transporters, including Mrp2 and p-glycoprotein, are expressed at the transcript level.

Figure 7:
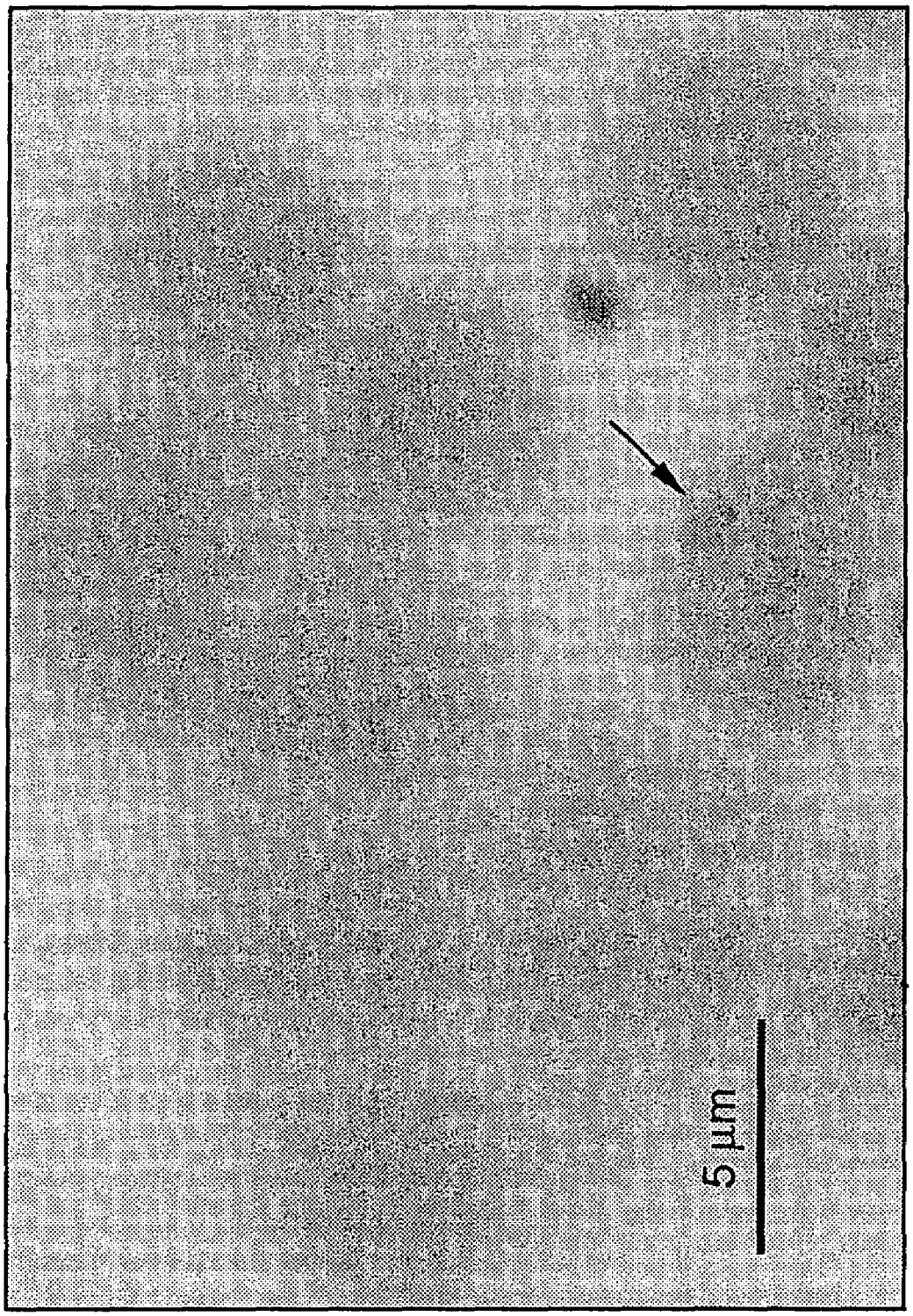
FIG. 7. *Plasmodium falciparum* trophozoite was observed in blood smear preparation after adding human red cell to the culture on day 21 and harvesting red cell 24 hours later.
Figure 8:
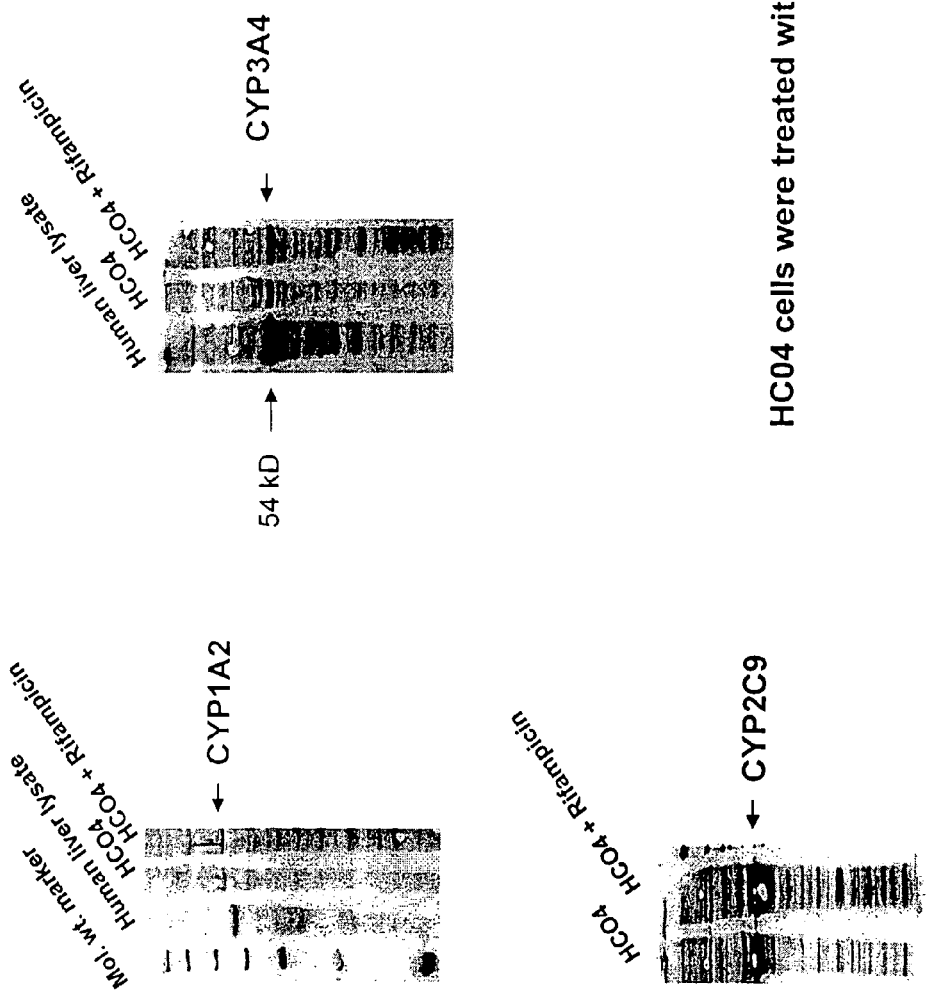
FIG. 8. Expression of human CYP isoforms in HC04 cells. HC04 cells were treated with 50 uM rifampicin for 24 hrs.
Figure 9:
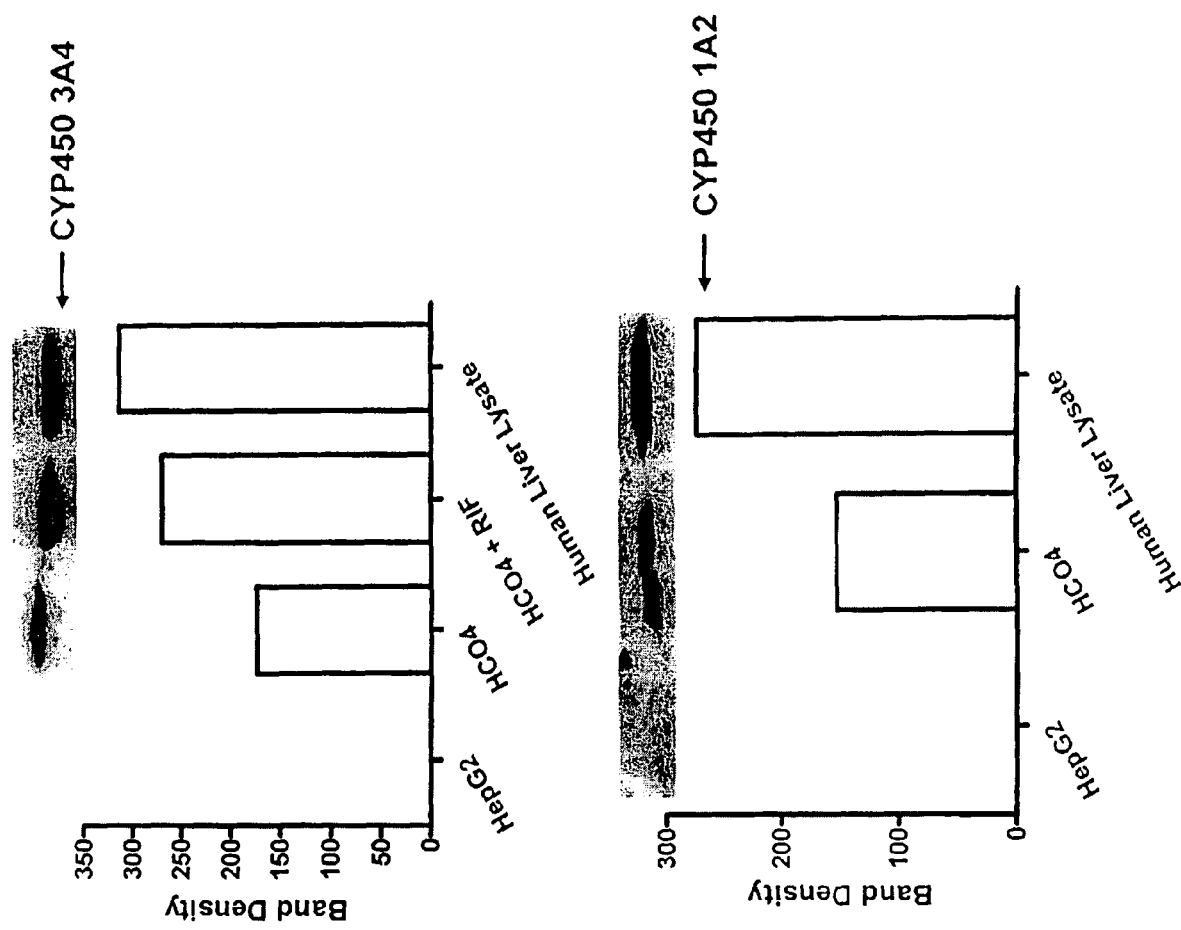
FIG. 9. Densitometric analysis of CYP isoform expression in HepG2 and HC04 cells and human liver lysate.

To identify whether this translates to protein expression, a number of CYPs were assessed by Western immunoblotting (FIG. 7). The quantitatively and qualitatively most important form, CYP3A4, is expressed in HC04, but also CYP1A2 and CYP2C9, all of which are important in drug metabolism. Importantly, the cells retain the ability to upregulate expression of these CYPs as shown by treatment of HC04 cells with the human-selective inducer, rifampicin (50 uM) for 24-48 h. Both CYP3A4 and 2C9 could be induced, which is in line with the observed expression of PXR mRNA.

Studies on the actual drug-metabolizing activity of some of the CYPs are ongoing (midazolam 1'-hydroxylation as a probe for CYP3A4). The rate of metabolism will be assessed by analyzing cell cultures plus supernatant by HPLC, and the rates will be compared with those in HepG2 and primary human hepatocytes.

TABLE 1

Summary of RT-PCR result

| | Hep G2 | Huh7 | HC04 | Hepatocytes |
|---|---|---|---|---|
| SULT1A1 | + | + | + | + |
| SULT1A2 | ++ | ++ | nd | nd |
| SULT1A3 | +++ | +++ | +++ | ++ |
| SULT1B1 | − | − | + | − |
| SULT1C1 | + | − | + | − |
| SULT2A1 | + | − | +++ | + |
| MRP1 | ++ | ++ | + | + |
| MRP2 | ++ | ++ | ++ | ++ |
| MRP3 | + | + | + | + |
| MRP4 | + | + | + | + |
| MRP5 | ++ | ++ | ++ | ++ |
| MRP6 | + | ++ | +++ | ++ |
| OATP-B | + | ++ | +++ | − |
| OTAP-E | +++ | − | +++ | − |
| P-gp | ++ | ++ | + | ++ |
| MDR3 | +++ | +++ | ++ | ++ |
| BSEP | − | ++ | − | ++ |

TABLE 1-continued

Summary of RT-PCR result

| | Hep G2 | Huh7 | HC04 | Hepatocytes |
|---|---|---|---|---|
| CYP1A1 | ++ | ++ | − | + |
| CYP3A5 | + | + | ++ | ++ |
| UGT1A6 | + | + | +++ | + |
| GSTA1 | + | − | ++ | + |
| GSTA2 | + | − | ++ | − |
| GSTA4 | ++ | + | ++ | + |
| GSTM1 | − | + | − | + |
| GSTP1 | − | +++ | − | + |
| PXR | + | + | + | ++ |
| GR a | +++ | +++ | ++ | +++ |
| GR b | + | + | + | + |
| RXR a | + | ++ | ++ | − |
| HNF3B | + | + | + | − |
| HNF4A | +++ | +++ | ++ | + |
| HNF4G | ++ | ++ | ++ | + |

Abbreviations:
SULT Sulfotransferase (phase II enzyme)
MRP Multidrug resistance-associated protein (transporter)
OATP Organic anion transporting peptide
P-gp P-glycoprotein (transporter)
MDR Multidrug resistance protein (transporter)
BSEP Bile salt transporting protein
CYP Cytochrome P450
UGT UDP-glucuronosyltransferase (phase II enzyme)
GST Glutathione-S-transferase (phase II enzyme)
PXR Pregnane X receptor (transcription factor regulating CYPs and transporters)
GR Glucocorticoid receptor
RXR Retinoic X receptor (partner for transcription factor)
HNF Hepatocyte nuclear factor (transcription factor)

EXAMPLE 4

To determine whether HC04 cells would respond to a standard hepatotoxicant in vitro, the concentration- and time-dependent toxicity of acetaminophen (APAP) was assessed and compared to that in HepG2 cells. HC04 cells exhibited increased LDH release (indicative of cell injury) with 500 uM APAP after 48 h, while HepG2 cells did not respond to APAP. This result is an indirect measure for the demonstration of intact drug-bioactivating and downstream signaling pathways in HC04 cells.

One of the advantages of using HC04 cells (over other cell lines) is that they are relatively close to primary human hepatocytes. A major advantage of HC04 in comparison with primary human hepatocytes is that they are readily available, and that multiple serial experiments can be performed with identical cells (low variability) in well characterized cells.

EXAMPLE 5

Leflunomide is a Potent Inhibitor of the Mitochondrial Permeability Transition Pore Leflunomide (LEF), a novel disease-modifying anti-rheumatic drug in the treatment of rheumatoid arthritis and autoimmune disease, has been associated with rare idiosyncratic liver injury in patients. The mechanisms are not known, but mitochondria could be a potential target. Because LEF is an inhibitor of dihydroorotate dehydrogenase, a protein linked to the mitochondrial electron transport chain which in turn regulates the membrane permeability transition (mPT), we hypothesized that LEF may interfere with mitochondrial function.

To explore whether LEF (the prodrug) or its active metabolite A77-1726 alter mitochondrial function including the $Ca^{2+}$ dependent, cyclosporine A-sensitive mPT, we isolated mouse liver mitochondria and exposed them to LEF or A77-1726, and measured the concentration-dependent effects on the mitochondrial inner transmembrane potential ($\Delta\Psi_m$) using the cationic fluorescent probe, JC-1. Furthermore, the effects on the inductin of the mPT were assessed by monitoring large amplitude swelling at 540 nm. In addition, the effects of LEF were determined in cultured immortalized human hepatocytes (HC04 cell line).

Both LEF and A77-1726 attenuated the $\Delta\Psi_m$ (at $\geq 1$ uM). Furthermore, LEF completely protected from the mPT caused by nimesulide (30 uM) or $KH_2PO_4$ (2 mM). In line with these data, LEF protected from mPT-mediated cytochrome c release from mitochondria. Finally, LEF completely protected from acetaminophen-induced mPT-associated cytotoxicity in cultured human hepatocytes.

Our results indicate that both LEF and its active metabolite are weak uncouplers but potent inhibitors of the mPT in vitro. This is consistent with our hypothesis that LEF targets mitochondria and alters mitochondrial function.

What is claimed is:

1. A method for screening a compound affecting malaria parasite development in a human liver cell infected with said parasite comprising
    incubating components comprising the compound and at least one immortalized normal human hepatocyte which has been infected with the parasite under conditions sufficient to allow the compound and cell to interact; and
    determining the effect of the compound on the parasite.

2. The method of claim 1 wherein said immortalized normal human hepatocyte is from HC-04.

3. The method of claim 2 wherein said malaria parasite is *P. falciparum* or *P. vivax*.

4. A method for screening a compound affecting a normal human liver cell infected with a malaria parasite:
    incubating components comprising the compound and at least one immortalized normal human hepatocyte infected with the parasite under conditions sufficient to allow the compound and cell to interact; and
    determining the effect of the compound on the cell.

5. The method of claim 4 wherein said immortalized normal human hepatocyte is from HC-04.

6. The method of claim 5 wherein said malaria parasite is *P. falciparum* or *P. vivax*.

* * * * *